United States Patent
Taylor et al.

(10) Patent No.: US 9,977,066 B2
(45) Date of Patent: May 22, 2018

(54) SYSTEMS, METHODS, AND DEVICES FOR DIAGNOSING INTEGRITY OF ELECTRICAL CONDUCTOR-CARRYING SYSTEMS

(71) Applicants: Jesse Wade Taylor, Baldwinsville, NY (US); Joseph Michael Manahan, Manlius, NY (US)

(72) Inventors: Jesse Wade Taylor, Baldwinsville, NY (US); Joseph Michael Manahan, Manlius, NY (US)

(73) Assignee: Cooper Technologies Company, Houston, TX (US)

( * ) Notice: Subject to any disclaimer, the term of this patent is extended or adjusted under 35 U.S.C. 154(b) by 145 days.

(21) Appl. No.: 14/687,367

(22) Filed: Apr. 15, 2015

(65) Prior Publication Data

US 2016/0306001 A1     Oct. 20, 2016

(51) Int. Cl.
*G01R 31/02* (2006.01)
*G01N 27/00* (2006.01)
*G01N 17/00* (2006.01)

(52) U.S. Cl.
CPC ........... *G01R 31/025* (2013.01); *G01N 27/00* (2013.01); *G01R 31/021* (2013.01); *G01R 31/024* (2013.01); *G01N 17/00* (2013.01)

(58) Field of Classification Search
CPC .......................... G01R 31/021; G01R 31/025
USPC ........................................................ 324/509
See application file for complete search history.

(56) References Cited

U.S. PATENT DOCUMENTS

| | | | | |
|---|---|---|---|---|
| 4,099,117 A | * | 7/1978 | Erath | G01N 27/205 |
| | | | | 324/357 |
| 4,393,711 A | * | 7/1983 | Lapides | G01H 1/00 |
| | | | | 73/1.82 |
| 4,400,782 A | * | 8/1983 | Ishikawa | C23F 13/04 |
| | | | | 324/323 |
| 4,471,294 A | | 9/1984 | Nielsen | |

(Continued)

FOREIGN PATENT DOCUMENTS

| | | |
|---|---|---|
| CN | 201724978 | 1/2011 |
| KR | 101459623 | 7/2014 |

(Continued)

OTHER PUBLICATIONS

K. Loshkov, International Search Report and Written Opinion in International Application No. PCT/US2016/027687, completion date Jul. 7, 2016, dated Aug. 25, 2016, 7 pages.

(Continued)

*Primary Examiner* — Walter L Lindsay, Jr.
*Assistant Examiner* — Milton Gonzalez
(74) *Attorney, Agent, or Firm* — King & Spalding LLP

(57) ABSTRACT

A system for diagnosing integrity of an electrical conductor-carrying system can include an electrical conductor-carrying network having a number of electrical conductor-carrying devices mechanically coupled to each other, where at least a portion of the electrical conductor-carrying network is made of electrically conductive material. The system can also include a number of sensor modules coupled to the electrical conductor-carrying network. The system can further include a control unit communicably coupled to the sensor modules. The sensor modules can measure at least one impedance in the electrical conductor-carrying devices of the electrical conductor-carrying network.

16 Claims, 7 Drawing Sheets

(56) References Cited

U.S. PATENT DOCUMENTS

| | | | | |
|---|---|---|---|---|
| 4,611,175 | A | * | 9/1986 | Kumar .................. G01N 17/02 204/404 |
| 4,884,034 | A | | 11/1989 | Guzman |
| 5,087,873 | A | * | 2/1992 | Murphy .................. G01V 3/06 204/196.06 |
| 5,529,668 | A | * | 6/1996 | Hall ....................... G01N 17/02 204/404 |
| 5,708,195 | A | | 1/1998 | Kurisu et al. |
| 6,265,880 | B1 | * | 7/2001 | Born ....................... G01R 27/08 324/525 |
| 6,843,137 | B2 | | 1/2005 | Keech |
| 7,323,880 | B2 | | 1/2008 | Stitt |
| 7,965,085 | B2 | | 6/2011 | Blakely |
| 8,220,484 | B2 | | 7/2012 | Howitt |
| 2004/0065377 | A1 | * | 4/2004 | Whiteley ............... F16L 11/127 138/104 |
| 2009/0212965 | A1 | * | 8/2009 | Becattini | |
| 2011/0058300 | A1 | * | 3/2011 | Krauss | |
| 2011/0241891 | A1 | | 10/2011 | Tong |
| 2012/0150460 | A1 | | 6/2012 | Balcerek et al. |
| 2013/0333474 | A1 | | 12/2013 | Godfrey et al. |
| 2014/0084687 | A1 | | 3/2014 | Dent |

FOREIGN PATENT DOCUMENTS

| | | |
|---|---|---|
| RU | 112525 | 1/2012 |
| WO | 2014088562 | 6/2014 |

OTHER PUBLICATIONS

Machine translation of RU112525 via LexisiNexis Total Patent, 5 pages.
Machine translation of CN201724978 via LexisiNexis Total Patent, 4 pages.

* cited by examiner

SYSTEMS, METHODS, AND DEVICES FOR DIAGNOSING INTEGRITY OF ELECTRICAL CONDUCTOR-CARRYING SYSTEMS

TECHNICAL FIELD

The present disclosure relates generally to networks that carry electrical conductors, and more particularly to systems, methods, and devices for diagnosing the integrity of electrical conductor-carrying systems or devices.

BACKGROUND

Many commercial and industrial facilities have conduit systems that distribute power. These conduit systems are electrically coupled to ground (e.g., Earth ground). It is safety critical that these conduit systems maintain an active and good ground connection. Such systems can also, or in the alternative, include other devices that carry electrical conductors. Such other devices can include, but are not limited to, cable glands, armored cables, and electrical connectors. Systems installed in harsh and hazardous locations are susceptible to corrosion, vibration, and/or other factors that lead to the deterioration of the system, for example in terms of grounding continuity. In such a case, if the conduit grounding circuit is compromised, a significant spark, shorting event, or other adverse electrical condition could occur, leading to potentially catastrophic consequences.

SUMMARY

In general, in one aspect, the disclosure relates to a system for diagnosing integrity of an electrical conductor-carrying system. The system can include an electrical conductor-carrying network having a number of electrical conductor-carrying devices mechanically coupled to each other, where at least a portion of the electrical conductor-carrying devices is made of electrically conductive material. The system can also include a number of sensor modules coupled to the electrical conductor-carrying network. The system can further include a control unit communicably coupled to the sensor modules. The sensor modules can measure at least one impedance in the electrical conductor-carrying devices of the electrical conductor-carrying network.

In another aspect, the disclosure can generally relate to a sensor module. The sensor module can include a body configured to be coupled to a section of an electrical conductor-carrying network. The sensor module can also include a sensor disposed within the body, where the sensor is configured to measure an impedance in electrical conductor-carrying device adjacent to the section in the electrical conductor-carrying network. The sensor module can further include a communication device communicably coupled to the sensor.

In yet another aspect, the disclosure can generally relate to a method for evaluating a grounding state of an electrical conductor-carrying network. The method can include coupling a number of sensor devices to the electrical conductor-carrying network, where each sensor device measures at least one impedance in a portion of the electrical conductor-carrying network. The method can also include collecting a number of measurements taken by the plurality of sensor devices. The method can further include comparing the measurements with at least one threshold value. The method can also include identifying, when at least one of the plurality of measurements exceeds the at least one threshold value, a target zone in the electrical conductor-carrying network, where the target zone includes an adverse electrical condition.

These and other aspects, objects, features, and embodiments will be apparent from the following description and the appended claims.

BRIEF DESCRIPTION OF THE DRAWINGS

The drawings illustrate only example embodiments and are therefore not to be considered limiting in scope, as the example embodiments may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

DETAILED DESCRIPTION

Figure 1:
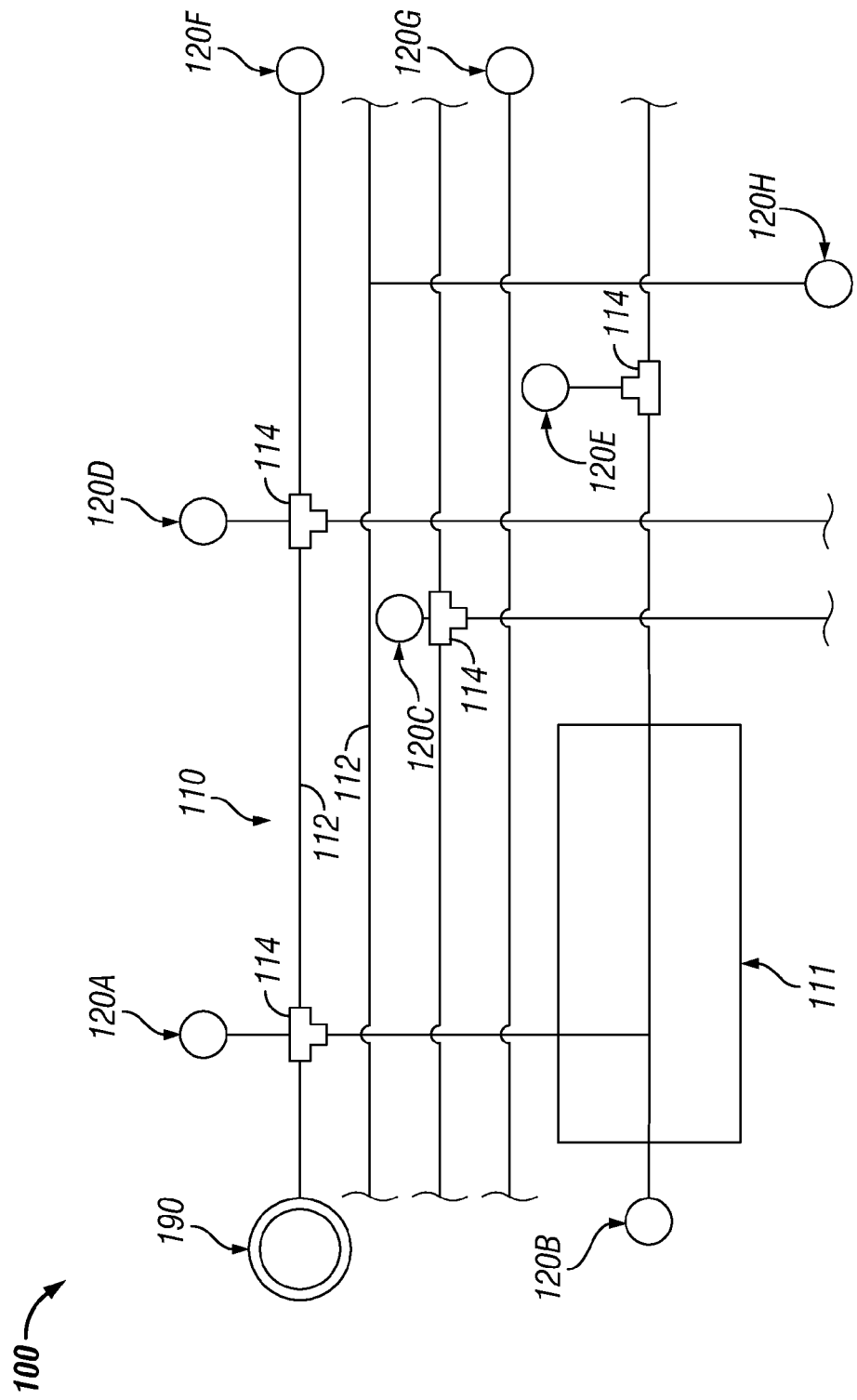
FIG. 1 shows a diagram of an electrical conductor-carrying system in accordance with certain example embodiments.

In general, example embodiments provide systems, methods, and devices for diagnosing the integrity of systems and/or devices that carry electrical conductors. Example systems, methods, and devices for diagnosing the integrity of systems and/or devices that carry electrical conductors provide a number of benefits. Such benefits can include, but are not limited to, ease of installation, ease of operation, portability of some or all of the system, indication of a grounding issue with a system or device that carries (houses) electrical conductors, providing notification of a water leak, providing notification of a health concern, and pinpointing a particular problem area in a system or device that houses electrical conductors.

Example embodiments can be used detect corrosion and/or loosening connections in an electrical conductor-carrying system. Detecting such conditions can lead the avoidance of one or more adverse consequences. An adverse consequence can be an event or condition that has a direct impact on the electrical conductor-carrying system (e.g., a risk of electrical shock to a user caused by an improper ground that isolates a portion of a system, damage to an electrical conductor caused by separation of conduit) or some other adverse impact (e.g., corrosion in conduit that causes contamination in a food and beverage plant). In other words, example embodiments can be used to detect the occurrence or the likelihood of an occurrence of one or more adverse conditions that are caused, directly or indirectly, by a problem (e.g., corrosion, vibrations) with an electrical conductor-carrying system.

The example embodiments discussed herein can be directed to a system or devices that house electrical conductors and are used in any type of application (e.g., a PV solar system, generation control systems, branch circuit management and protection). A user may be any person that interacts with such systems or devices. Examples of a user may include, but are not limited to, an engineer, an electrician, an instrumentation and controls technician, a mechanic, an operator, a consultant, a contractor, and a manufacturer's representative.

The systems, methods, and devices for diagnosing the integrity of an electrical conductor-carrying system (or components thereof) described herein can be made of one or more of a number of suitable materials to allow an electrical conductor-carrying system to meet certain standards and/or regulations while also maintaining durability in light of the one or more conditions under which the electrical conductor-carrying system, including the example devices (e.g., sensing modules) used for diagnosing the integrity of the electrical conductor-carrying system, can be exposed. Examples of such materials can include, but are not limited to, aluminum, stainless steel, fiberglass, glass, plastic, ceramic, and rubber.

Example sensing modules, or portions thereof, described herein can be made from a single piece (as from a mold, injection mold, die cast, or extrusion process). In addition, or in the alternative, example sensing modules, or portions thereof, can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, mounting, fastening, securing, or other similar terms. Such terms are merely meant to distinguish various elements and/or features within a component or device and are not meant to limit the capability or function of that particular element and/or feature. For example, a feature described as a "coupling feature" can couple, mount, secure, fasten, and/or perform other functions aside from merely coupling.

A coupling feature (including a complementary coupling feature) as described herein can allow one or more components and/or portions of an example electrical conductor-carrying system (e.g., a sensing module, a control unit) to become mechanically coupled, directly or indirectly, to another portion (e.g., conduit pipe, electrical enclosure) of the electrical conductor-carrying system. A coupling feature can include, but is not limited to, a portion of a hinge, an aperture, a recessed area, a protrusion, a clamp, a slot, a spring clip, a tab, a detent, and mating threads. One component or portion of an example electrical conductor-carrying system can be coupled to another component or portion of the electrical conductor-carrying system by the direct use of one or more coupling features.

In addition, or in the alternative, a component or portion of an example electrical conductor-carrying system can be coupled to another component or portion of the electrical conductor-carrying system using one or more independent devices that interact with one or more coupling features disposed on a component or portion of the electrical conductor-carrying system. Examples of such devices can include, but are not limited to, a pin, a hinge, a fastening device (e.g., a bolt, a screw, a rivet), and a spring. One coupling feature described herein can be the same as, or different than, one or more other coupling features described herein. A complementary coupling feature as described herein can be a coupling feature that mechanically couples, directly or indirectly, with another coupling feature.

Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is a three digit number and corresponding components in other figures have the identical last two digits.

In the foregoing figures showing example embodiments of systems, methods, and devices for diagnosing the integrity of an electrical conductor-carrying system, one or more of the components shown may be omitted, repeated, and/or substituted. Accordingly, example embodiments of systems, methods, and devices for diagnosing the integrity of electrical conductor-carrying systems should not be considered limited to the specific arrangements of components shown in any of the figures. For example, features shown in one or more figures or described with respect to one embodiment can be applied to another embodiment associated with a different figure or description.

As defined herein, an electrical conductor-carrying system includes one or more electrical conductor-carrying devices. An electrical conductor-carrying device is any type of cabinet or housing inside of which is disposed one or more electrical conductors. An electrical conductor is a length of electrically conductive material that carries a power, control, communication, and/or ground signal from one end of the electrical conductor to the other end of the electrical conductor. In some cases, an electrical conductor can generate heat when operating.

Examples of an electrical conductor-carrying device can include, but are not limited to, an electrical connector, an electrical enclosure, the armor of an armored cable, a cable gland, a cable tray, a junction box, a Condulet®, an outlet box, a motor control center, a breaker cabinet, an electrical housing, a conduit pipe or network, a control panel, an indicating panel, and a control cabinet. (Condulet is a registered trademark of Cooper Technologies Company incorporated in Delaware and located at 600 Travis Street, Houston, Tex. 77002.) In certain example embodiments, an electrical conductor-carrying device is made of one or more electrically conductive materials. In some cases, one or more electrical conductor-carrying devices in an electrical conductor-carrying system do not have, or are not designed to have, an electrical conductor disposed therein. For purposes of this application, an electrical conductor-carrying device can have no electrical conductor disposed therein, either by design or by a user's choice.

In certain example embodiments, electrical conductor-carrying systems (e.g., conduit systems) are subject to meeting certain standards and/or requirements. For example, the National Electric Code (NEC), Underwriters Laboratories (UL), the American National Standards Institute (ANSI), the National Electrical Manufacturers Association (NEMA), the International Electrotechnical Commission (IEC), and the Institute of Electrical and Electronics Engineers (IEEE) set standards as to electrical enclosures, wiring, and electrical connections. For example, ANSI/NEMA FB 1 are standards that apply to fittings, cast metal boxes and conduit bodies for conduit, electrical metallic tubing, and cable. Use of example embodiments described herein meet (and/or allow a corresponding device to meet) such standards when required.

In some applications, additional standards particular to that application may apply to the systems described herein. For example, electrical conductor-carrying systems can be located in hazardous and/or marine environments. Examples of a hazardous location in which example embodiments can be used can include, but are not limited to, an airplane hangar, a drilling rig (as for oil, gas, or water), a production rig (as for oil or gas), a refinery, a chemical plant, a power plant, a mining operation, a wastewater treatment facility, and a steel mill. A hazardous environment can include an explosion-proof environment, which would require portions of an electrical conductor-carrying system to meet one or more requirements, including but not limited to flame paths having certain tolerances and configurations.

As stated above, it is safety critical that electrical conductor-carrying systems (and, more specifically, electrical conductor-carrying networks of electrical conductor-carrying systems) maintain an active and solid ground connection. Regardless of the environment, but particularly in certain hazardous environments (e.g., high vibrations, corrosive environments), ground connections of an electrical conductor-carrying system can degrade and deteriorate over time. When this degradation and deterioration occurs beyond a certain extent, ground continuity can be lost in the system, which can isolate an electrical circuit in a phase-to-ground condition and fall outside a protective scheme (e.g., relays, circuit breakers) designed to protect the electrical circuit. As a result, adverse electrical conditions (e.g., risk of shock, overcurrent conditions) can occur, resulting in loss of equipment and/or jeopardizing the safety of personnel.

Example embodiments are designed to identify the degradation and deterioration of ground connections for an electrical conductor-carrying system. In addition, example embodiments can provide a user with a specific location in the electrical conductor-carrying system where the degradation and deterioration of a ground connection is occurring. This allows for ease in maintenance and correcting issues with a ground connection of an electrical conductor-carrying system before an adverse electrical condition occurs. Example embodiments can also provide early detection of degradation and deterioration of a ground connection in an electrical conductor-carrying system based on multiple measurements taken by the sensors over time. Also, as stated above, example embodiments can detect conditions that can lead to adverse conditions (e.g., risk of contamination) that are not directly related to an electrical system or electrical conductors feeding such an electrical system. The example sensor modules can remain permanently in place relative to the electrical conductor-carrying system, or sensor modules can be portable and reconfigured by a user. In the latter case, one set of sensor modules can be used to monitor and diagnose a number of electrical conductor-carrying systems or multiple portions of a large electrical conductor-carrying system.

Example embodiments of systems, methods, and devices for diagnosing electrical conductor-carrying system integrity will be described more fully hereinafter with reference to the accompanying drawings, in which example embodiments of systems, methods, and devices for diagnosing electrical conductor-carrying system integrity are shown. Systems, methods, and devices for diagnosing electrical conductor-carrying system integrity may, however, be embodied in many different forms and should not be construed as limited to the example embodiments set forth herein. Rather, these example embodiments are provided so that this disclosure will be thorough and complete, and will fully convey the scope of systems, methods, and devices for diagnosing electrical conductor-carrying system integrity to those of ordinary skill in the art. Like, but not necessarily the same, elements (also sometimes called components) in the various figures are denoted by like reference numerals for consistency.

Terms such as "first", "second", "top", "bottom", "side", "width", "length", "inner", "outer", "left", and "right" are used merely to distinguish one component (or part of a component or state of a component) from another. Such terms are not meant to denote a preference or a particular orientation, and are not meant to limit embodiments of systems, methods, and devices for diagnosing electrical conductor-carrying system integrity. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

FIG. 1 shows a diagram of an electrical conductor-carrying system 100 in accordance with certain example embodiments. The system 100 of FIG. 1 includes an electrical conductor-carrying network 110, a number of example sensor modules 120, and a control unit 190. The electrical conductor-carrying network 110 can include multiple electrical conductor-carrying devices, which in this example are conduit pipes 112 (also more generically called conduit) and electrical connectors 114. In this case, a conduit pipe 112 can be coupled to at least one adjacent conduit pipe 112 and/or any other suitable electrical enclosure 114. In another example, one or more of the conduit pipe 112 can be replaced with one or more of number of other electrical conductor-carrying devices, such as an armored cable, and one or more of the electrical enclosures 114 can be replaced with one or more of a number of other electrical conductor-carrying devices, such as a cable gland.

Each conduit pipe 112 can be tubular in shape, having a wall that forms a cavity that traverses the length of the conduit pipe 112. A conduit pipe 112 can be of any of a number of materials, including but not limited to metal, plastic, fiber, composite materials, and clay. In addition, or in the alternative, a conduit pipe 112 can be rigid or flexible. When a conduit pipe 112 is made of electrically conductive material, certain standard-setting entities (e.g., the NEC) can require a permanent and continuous path through the conduit pipe 112 to ground (e.g., Earth ground).

One or more electrical cables can be pulled through and disposed within the cavity of an electrical conductor-carrying device, such as the conduit pipe 112. As defined herein, an electrical cable can be used to conduct power (e.g., high voltage) and/or control (e.g., low voltage) signals. Power flowing through an electrical cable can be alternating current or direct current. Each electrical cable can carry voltage and/or current from one end of the electrical cable to the other end. Each electrical cable can have one or more electrical conductors disposed therein. In some cases, an electrical cable can include a ground or neutral conductor, through which no (or negligible) current or voltage flows. Each electrical conductor within an electrical cable may be of any suitable size (e.g., 12 American Wire Gauge (AWG)) and made of one or more of a number of materials (e.g., copper, aluminum). Each electrical cable may be coated with an insulator made of any suitable material (e.g., rubber, plastic) to keep the electrical conductors electrically isolated from any other conductor in the electrical cable.

In certain example embodiments, the electrical conductor-carrying network 110 also includes one or more other types of electrical conductor-carrying devices, such as an electrical enclosure 114, aside from conduit pipe 112. In such a case, the electrical enclosure 114 can include a cover. When the cover of the electrical enclosure 114 is removed, an electrical cable and/or other electrical equipment disposed within the electrical enclosure 114 can be accessed. For example, removing the cover of an electrical enclosure 114 can allow an electrical cable to be pulled through a conduit pipe 112 that is mechanically coupled to the electrical enclosure 114.

A conduit pipe 112 can be mechanically coupled to another conduit pipe 112 and/or an electrical enclosure 114. Specifically, one end of a conduit pipe 112 can be coupled to another conduit pipe 112 and/or an electrical enclosure 114, and the other end of the conduit pipe 112 can be coupled to another conduit pipe 112 and/or an electrical enclosure 114. As a result, each end of a conduit pipe 112 can include one or more of a number of coupling features that complement coupling features disposed on an adjacent component (e.g., another conduit pipe 112, an electrical enclosure 114) of the electrical conductor-carrying network 110.

Typically, each end of a conduit pipe 112 will have mating threads disposed thereon. For example, one end of a conduit pipe 112 can have mating threads disposed on an outer surface of the conduit pipe 112, and the other end of the conduit pipe 112 can have mating threads disposed on an inner surface of the conduit pipe 112. Similarly, in such a case, an electrical enclosure 114 can have mating threads that are configured to complement the mating threads of a conduit pipe 112 that couples to the electrical enclosure 114.

As mentioned above, the electrical conductor-carrying system 100 of FIG. 1 includes a number of example sensors 120. In this case, the electrical conductor-carrying system 100 includes sensor module 120A, sensor module 120B, sensor module 120C, sensor module 120D, sensor module 120E, sensor module 120F, sensor module 120G, and sensor module 120H. Each example sensor module 120 is coupled to the electrical conductor-carrying network 110 at a different point in the electrical conductor-carrying network 110. Put another way, each sensor module 120 is coupled to a different component (e.g., another conduit pipe 112, an electrical enclosure 114) of the electrical conductor-carrying network 110. A sensor module 120 can be coupled to a portion of the electrical conductor-carrying network 110 in one or more of a number of ways, including but not limited to mechanically, electrically, directly, indirectly, and communicably.

Figure 3A:
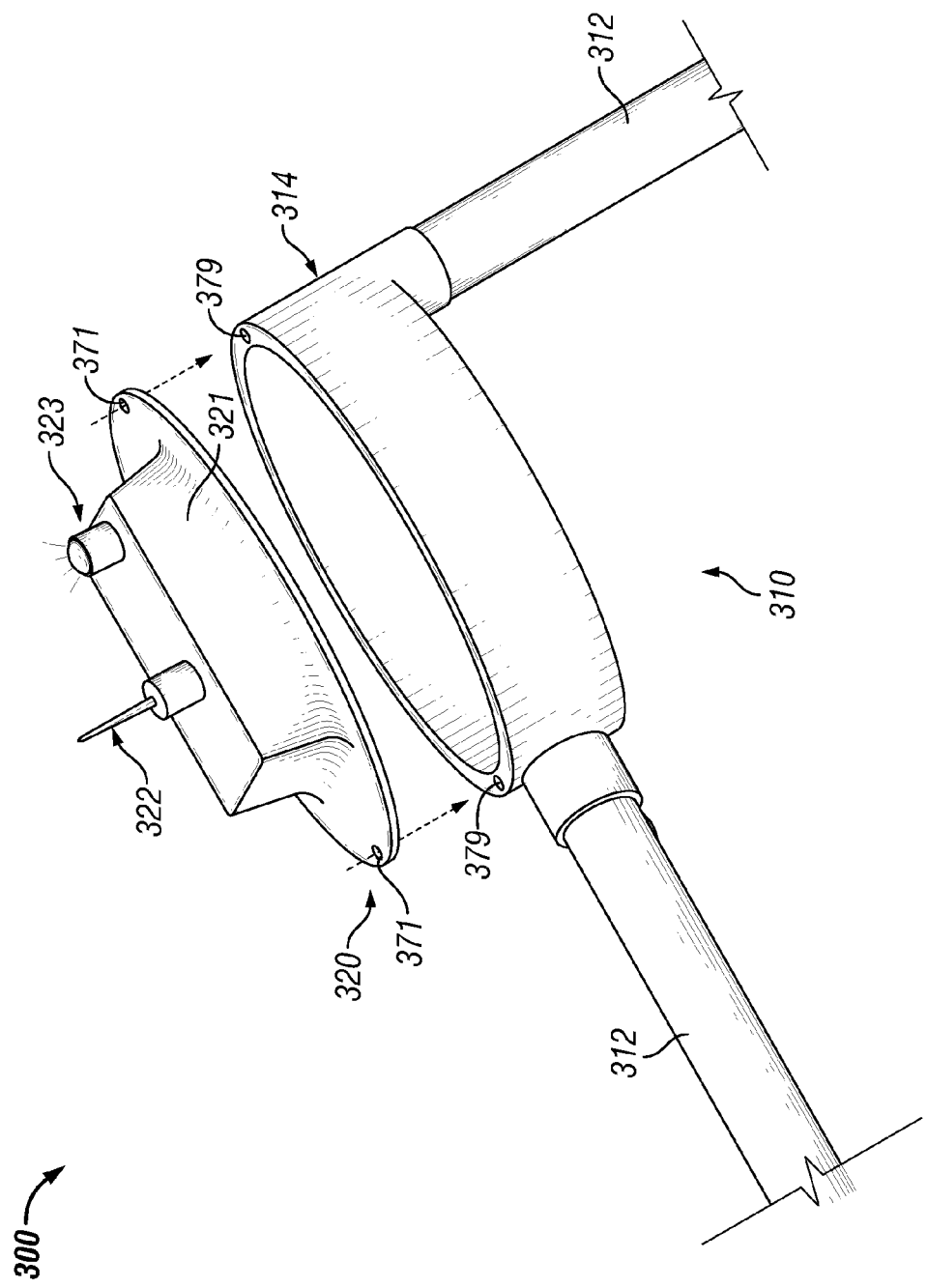
FIGS. 3A and 3B show a sensor module in accordance with certain example embodiments.
Figure 3B:
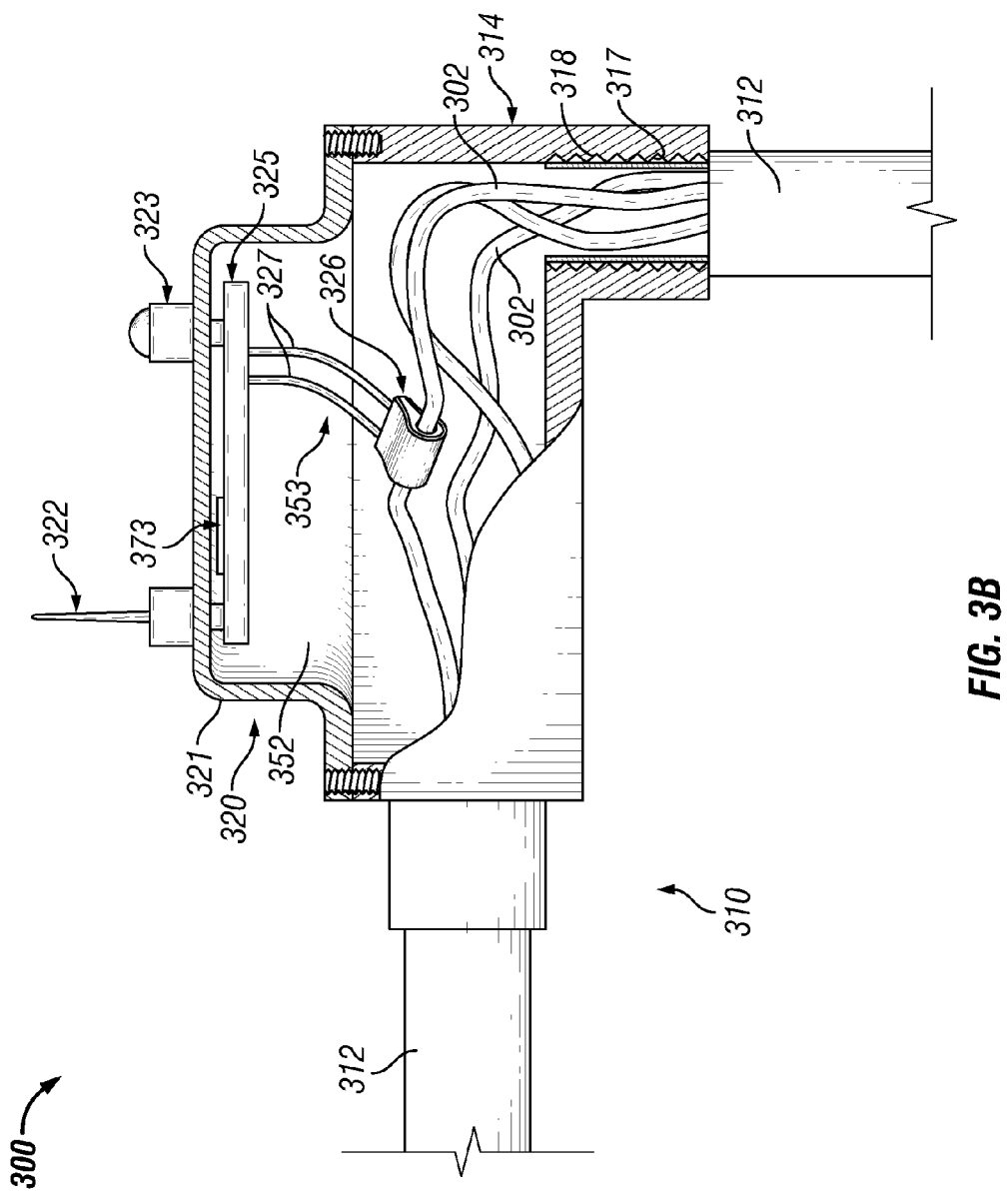

A sensor module 120 can be coupled to a component of the electrical conductor-carrying network 110 in any of a number of ways. For example, a sensor module 120 can be clamped over an outer surface of a conduit pipe 112 or an electrical enclosure 114. As another example, as shown in FIGS. 3A and 3B below, a sensor module 120 can be integrated with an electrical enclosure 114 in the electrical conductor-carrying network 110. As yet another example, a sensor module 120 can be positioned within a cavity of a component of the electrical conductor-carrying network 110.

As still another example, a sensor module 120 can include coupling features that complement the coupling features of a conduit pipe 112.

An example sensor module 120 can use electrical power to operate (e.g., measure an impedance, send a communication). The electrical power can be provided by any of a number of power sources, including but not limited to an energy storage device (e.g., a battery), a feed to a building, an electrical cable disposed within one or more components (e.g., conduit pipe 112, electrical enclosure 114) of the electrical conductor-carrying network 110, and an independent generation source (e.g., photovoltaic panels, a heat exchanger). Details of example sensor modules are provided below with respect to FIGS. 3A-4.

The multiple sensor modules 120 can be distributed throughout the electrical conductor-carrying network 110 and can identify one or more of a number of target zones 111 within the electrical conductor-carrying network 110. A target zone 111 can be some area of an electrical conductor-carrying network 110 where an adverse electrical condition is occurring and/or where the occurrence of an adverse electrical condition is becoming more likely based on degradation and deterioration of a ground connection of the electrical conductor-carrying network 110. In this case, there are eight sensor modules 120 distributed throughout the electrical conductor-carrying network 110.

Each sensor module 120 can measure one or more aspects of a portion of the electrical conductor-carrying network 110 that is located adjacent to the sensor module 120. Examples of an aspect of the electrical conductor-carrying network 110 that can be measured by a sensor module 120 can include, but are not limited to, an impedance, temperature, and vibration. Some aspects (e.g., impedance) are dependent upon certain characteristics (e.g., electrically conductive material in the conduit pipe 112) of the portion of the electrical conductor-carrying network 110 adjacent to the sensor module 120, while other aspects (e.g., vibration) are independent of the characteristics of the portion of the electrical conductor-carrying network 110 adjacent to the sensor module 120.

The example sensor modules 120 can include one or more of a number of other features, as well. For example, a sensor module 120 can include one or more solid state components (e.g., a hardware processor, an integrated circuit) that operate some or all of the sensor module 120. As another example, a sensor module 120 can be self-calibrating. As a result, a sensor module 120 can be substantially free of maintenance for long periods of time, and the sensor module 120 can provide indication to a user, through the control unit 190, when the sensor module 120 is beginning to fail or has failed performing. Further, when a sensor module 120 is self-calibrating, the sensor module 120 can be moved from one electrical conductor-carrying network to another electrical conductor-carrying network and provide accurate measurements at each location.

As yet another example, the sensor modules 120 can have communication capability. In such a case, a sensor module 120 in the electrical conductor-carrying network 110 can communicate with (send data to and/or receive data from) the control unit 190 and/or one or more other sensor modules 120. A sensor module 120 can also store data (e.g., sensor measurements) for some period of time.

In certain example embodiments, the control unit 190 of the electrical conductor-carrying system 100 communicates with some or all of the sensor modules 120. The communication between the control unit 190 and a sensor module 120 can be performed using wired or wireless technology.

Wired technology can include, but is not limited to, dedicated electrical cables and use of existing electrical cables disposed in the electrical conductor-carrying network. Wireless technology can include, but is not limited to, visible light communication (also called VLC), HART, wireless HART, ISA100, and Wi-Fi.

The control unit 190 can send data (e.g., instructions) to one or more sensor modules 120. Examples of such data that the control unit 190 can send include, but are not limited to, taking a measurement, sending results of a measurement, turning on, entering sleep mode, and turning off. In addition, the control unit 190 can receive data from one or more sensor modules 120. Examples of such data that the control unit 190 can receive include, but are not limited to, results of a measurement and indication of a status of a sensor module 120.

In certain example embodiments, the control unit 190 collects data (e.g., measurements) from the sensor modules 120 in the electrical conductor-carrying system 100 and runs formulas and/or algorithms to identify one or more target zones (e.g., target zone 111), if any, where an adverse electrical condition exists or is likely to exist in the future. For the control unit 190 to effectively interpret the data received from the sensor modules 120, the control unit 190 can use other data (as provided by, for example, a user or a sensor module 120). Such other data can include, but is not limited to, the configuration of the electrical conductor-carrying network 110, the characteristics (e.g., material, wall thickness, inner diameter) of the various conduit pipe 112 in the electrical conductor-carrying network 110, threshold values (e.g., acceptable and unacceptable impedance values), the location of a sensing device 120 in the electrical conductor-carrying network 110, the characteristics (e.g., model number, manufacturer, type of sensor) of a sensing device 120, and the characteristics (e.g., frequency of signal for an impedance test, amplitude of signal sent, amplitude of signal received) of a sensor in the sensing device 120. Such data can be stored in memory in the control unit 190 or in a separate module or device that is communicably coupled with the control unit 190.

Further, the control unit 190 can interpret, in view of the other data at its disposal, the measurements taken by the sensor modules 120. The interpretation of the measurement data by the control unit 190 can be based on threshold values of those measurements. Further, the interpretation of the measurement data by the control unit 190 can be based on one or more measurements taken at a single point in time (instantaneous determination) or based on multiple measurements taken over a period of time. The thresholds used for an instantaneous determination can be the same as, or different than, the thresholds used for a determination made over time.

In certain example embodiments, the control unit 190 can communicate, using wired and/or wireless technology, with a user and/or a user system (e.g., a computer, a tablet, a mobile phone, a control room). As such, the control unit 190 can receive data (e.g., instructions, request for data) from the user and/or a user system. Examples of such data that the control unit 190 can receive from a user include, but are not limited to, a request for a sensor 120 to take a measurement, requesting results of a measurement, turning on, entering sleep mode, and turning off.

The control unit 190 can have a user interface (e.g., graphical user interface, display, pushbuttons, keyboard, switches) that allow a user to directly interact with the control unit 190. In addition, or in the alternative, the control unit 190 can communicate with a user system using wired or wireless technology using any of a number of communication protocols or methods (e.g., Internet, local area network wide area network, Ethernet cable, telephone lines, coaxial cable, fiber optic network). Similarly, the control unit 190 can communicate with one or more sensor modules 120 using such communication protocols or methods.

In addition, the control unit 190 can send data to the user and/or a user system. Examples of such data that the control unit 190 can send include, but are not limited to, measurements of one or more sensor modules 120, interpretations of such measurements (e.g., safe or unsafe condition of the electrical conductor-carrying network 110, indication of an emergency problem, indication of ground health of the electrical conductor-carrying network 110, location of a fault condition), and the status of a sensor module 120.

In certain example embodiments, the control unit 190 determines where the sensor modules 120 of an electrical conductor-carrying system 100 should be placed in the electrical conductor-carrying network 110 in order to more optimally monitor the electrical conductor-carrying network 110. This determination can be made based on data (e.g., configuration of the electrical conductor-carrying network 110, number of sensor modules 120, capabilities of the sensor modules 120) with respect to the electrical conductor-carrying system 100. In such a case, the control unit 190 can communicate its determination of the optimized configuration of the sensor modules 120 to a user so that the user can place the sensor modules 120 accordingly.

A control unit 190 for an electrical conductor-carrying system 100 can also communicate with another control unit 190 of another electrical conductor-carrying system 100. For example, a large electrical conductor-carrying system can be divided into multiple smaller electrical conductor-carrying systems, where each of these smaller electrical conductor-carrying systems can include a defined electrical conductor-carrying network, a control unit, and multiple sensor devices. In such a case, a control unit of one of these smaller electrical conductor-carrying systems can act as the control unit for that electrical conductor-carrying system as well as the control unit for the other control units of the other smaller electrical conductor-carrying systems.

An example control unit 190 can use electrical power to operate (e.g., send a communication, receive data, interpret data, report results, send notifications). The electrical power can be provided by any of a number of power sources, including but not limited to an energy storage device (e.g., a battery), a feed to a building, an electrical cable disposed within one or more components (e.g., conduit pipe 112, electrical enclosure 114) of the electrical conductor-carrying network 110, and an independent generation source (e.g., photovoltaic panels, a heat exchanger, a piezoelectric energy harvester).

Figure 2:
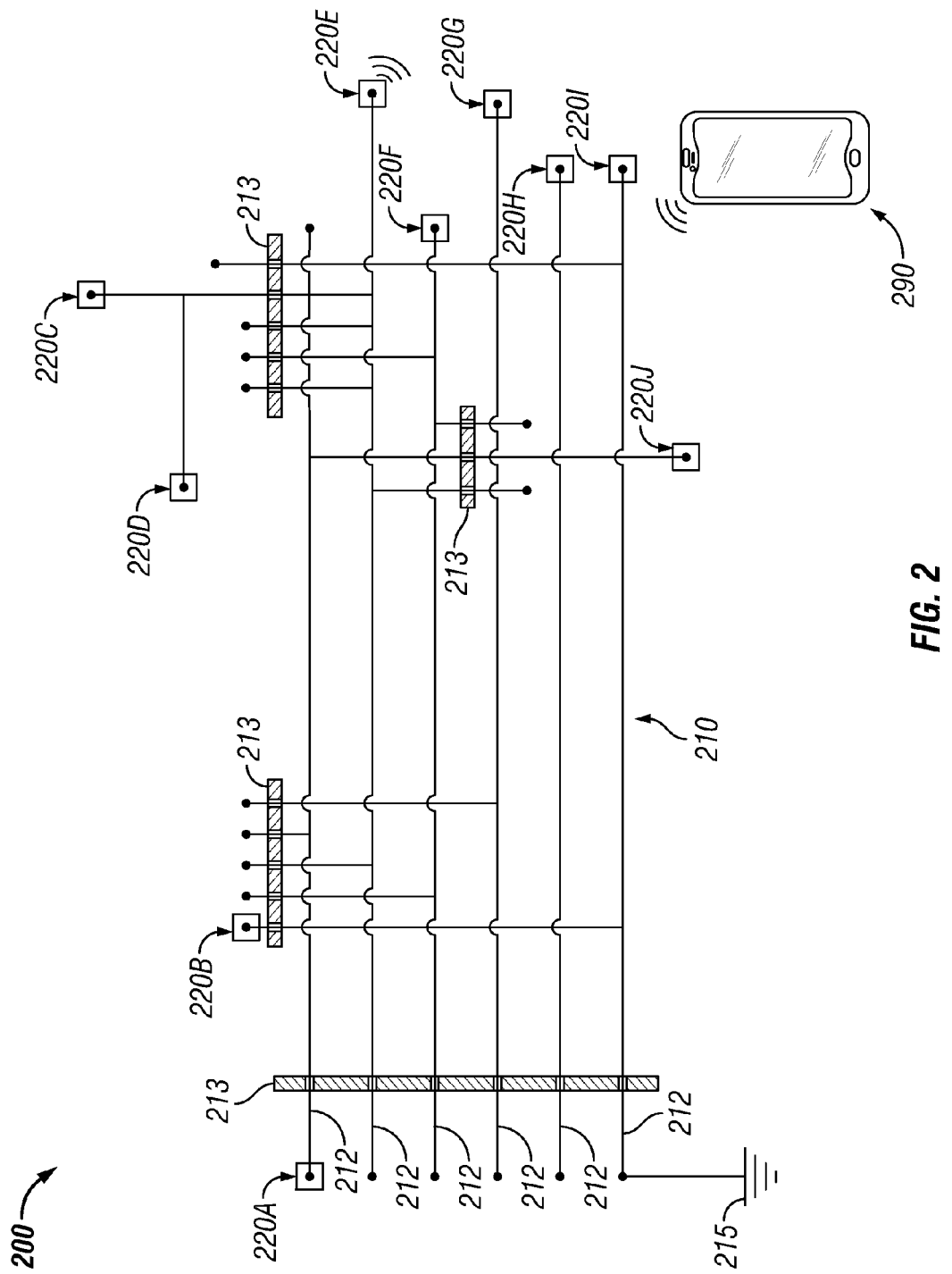
FIG. 2 shows a diagram of another electrical conductor-carrying system in accordance with certain example embodiments.

FIG. 2 shows a diagram of another electrical conductor-carrying system 200 in accordance with certain example embodiments. The electrical conductor-carrying system 200 of FIG. 2 is substantially the same as the electrical conductor-carrying system 100 of FIG. 1, except as described below. Referring to FIGS. 1 and 2, the electrical conductor-carrying system 200 has ten sensor modules 220 (sensor module 220A, sensor module 220B, sensor module 220C, sensor module 220D, sensor module 220E, sensor module 220F, sensor module 220G, sensor module 220H, sensor module 220I, and sensor module 220J) coupled to and distributed throughout the electrical conductor-carrying network 210.

Portions of the electrical conductor-carrying network 210 are supported by four different mounting structures 213

(e.g., brackets). Such mounting structures 213 can provide structural continuity and support for the electrical conductor-carrying network 210. In addition, or in the alternative, each mounting structure 213 can provide grounding continuity for the electrical conductor-carrying network 210. The system ground 215 for the electrical conductor-carrying network 210 is also shown in FIG. 2. The control unit 290 in this case is a mobile device (e.g., a cell phone) that is remote from the electrical conductor-carrying network 210 and communicates wirelessly with the sensor modules 220. While not expressly shown in FIG. 2, an electrical enclosure (such as the electrical enclosure 114 of FIG. 1) can be positioned at any of a number of locations in the electrical conductor-carrying network 210 where two or more conduit pipes 212 (or other electrical conductor-carrying devices) are joined.

FIGS. 3A and 3B show a portion of an electrical conductor-carrying system 300 that includes a sensor module 320 in accordance with certain example embodiments. In certain example embodiments, the sensor module 320 includes one or more of a number of features and/or components. For example, as shown in FIGS. 3A and 3B, the sensor module 320 can include a body 321, one or more sensors (e.g., sensor 373), a status indicator 323, an antenna 322, a printed circuit board 325, and a power conversion assembly 353. The body 321 can have at least one wall the forms a cavity 352, inside of which can be disposed one or more other components of the sensor module 320. The body 321 can form a closed cavity 352. Alternatively, as shown in FIGS. 3A and 3B, the body 321 can form an open cavity 352.

The body 321 can include one or more coupling features 371 that allow the body 321 to couple, directly or indirectly, to an electrical enclosure 314. For example, in this case, the coupling features 371 are apertures that traverse a portion of the body 321. The coupling features 371 can be aligned with corresponding coupling features 379 disposed in the electrical enclosure 314. In this example, the corresponding coupling features 379 disposed in the electrical enclosure 314 are also apertures that traverse at least a portion of the wall of the electrical enclosure 314. In such a case, one or more fastening devices (e.g., screws, bolts) can traverse the coupling features 371 of the body 321 of the sensor module 320 and the corresponding coupling features 379 of the electrical enclosure 314 to couple the sensor module 320 to the electrical enclosure 314.

As discussed above, the cover (not shown in FIGS. 3A and 3B) of the electrical enclosure 314 can be removable to allow a user access to one or more components (e.g., an electrical cable 302) of the electrical conductor-carrying system 300. In certain example embodiments, the shape, size, and/or configuration (e.g., placement and type of coupling features 371) of the body 321 of the sensor module 320 can be substantially the same as the corresponding features of a cover for the electrical enclosure 314. In this way, the sensing module 320 can replace the removable cover of the electrical enclosure 314.

Further, when the sensing module 320 is decoupled from the electrical enclosure 314, one or more components (e.g., the printed circuit board 325, the power conversion assembly 353) of the sensor module 320 can be accessible by a user. In some cases, when the original cover of the electrical enclosure 314 remains in place, the sensor module 320 can be disposed inside the cavity of the electrical enclosure 314. In this way, when the original cover of the electrical enclosure 314 is removed, one or more components of the sensor module 320 can be accessed by a user.

In any case, when the electrical enclosure 314 is located in certain environments (e.g., hazardous environments), the existing cover or the body 321 of the sensor module 320 can be engineered to comply with industry standards for an electrical enclosure in such an environment. For example, a flame path having certain tolerances between the body 321 of the sensor module 320 and the electrical enclosure 314 can allow the electrical enclosure 314 to be categorized as explosion-proof under NEMA standards.

The antenna 322 can be any communication transmission device that allows the sensor module 320 to communicate with another sensor module 320 and/or a control unit (e.g., control unit 290). The antenna 322 can be disposed in any of a number of locations relative to the body 321 of the sensor module 320 and/or have any of a number of configurations (e.g., shapes, sizes). For example, as shown in FIGS. 3A and 3B, the antenna 322 can be linear and protrude away from the top surface of the body 321 of the sensor module 320 at a substantially perpendicular angle relative to the top surface of the body 321. In certain example embodiments, the antenna 322 can have any orientation (e.g., protrude from the body 321 at a non-normal angle), shape, and size as appropriate for the antenna 322 to effectively send and receive signals. The antenna 322 can be considered to be, or can be part of, a communication device that is communicably coupled to the sensor 373 of the sensor module 320.

In certain example embodiments, the sensor module 320 also includes one or more indicator devices 323. Such indicator devices 323 can include, but are not limited to, an indicator light, a speaker, and a display. An indicator device 323 can be disposed at any point on or within the sensor module 320. For example, as shown in FIGS. 3A and 3B, the indicator device 323 can be an indicator light disposed on the top surface of the body 321 of the sensor module 320. When the status indicator 323 is a light source, the status indicator can communicate with another sensor module 320 and/or the control unit 190 using VLC.

The indicating device 323 can provide a notification to a user as to a problem with the sensor module 320 and/or the electrical conductor-carrying network 310 based on a measurement made by the sensor 373 of the sensor module 320. For example, the indicator device 323 of FIGS. 3A and 3B can activate (e.g., flash a red light) when the sensor 373 of the sensor module 320 measures an impedance in a conduit pipe 312 (or other electrical conductor-carrying device) of the electrical conductor-carrying network 310 that falls outside a range of acceptable impedance values. As another example, the indicator device 323 can activate (e.g., flash a yellow light) when the sensor 373 of the sensor module 320 measures an impedance in a conduit pipe 312 of the electrical conductor-carrying network 310 that falls at the high end of a range of acceptable impedance values.

In certain example embodiments, the power conversion assembly 353 of the sensor module 320 can act as a power source for the other components of the sensor module. In such a case, the power conversion assembly 353 can receive power and convert that power to a type and level of power used by the other components of the sensor module 320. The power conversion assembly 353 can include one or more of any of a number of power conversion devices, including but not limited to a transformer, an inductor, a converter, and an inverter. For example, in this case, the power conversion assembly 353 includes an inductor 326 that is disposed around (adjacent to) an electrical cable 302 (or a conductor of an electrical cable 302).

As power flows through the electrical cable 302 around which the inductor 326 is disposed, the inductor 326 induces power and sends the induced power through one or more conductors 327 of the power conversion assembly 353. The induced power can be of a type and amount that can be used to operate one or more other components (e.g., the indicating device 323, the sensor 373, a hardware processor) of the sensor module 320. In addition, or in the alternative, the power conversion assembly 353 can include one or more of a number of other components, including but not limited to a transformer, a resistor, a capacitor, a diode, and an integrated circuit. Such other components can be disposed on the circuit board 325, described below.

In certain example embodiments, the sensor module 320 includes one or more sensors 373, where each sensor 373 measures at least one parameter that affects the electrical conductor-carrying network 310. For example, as shown in FIGS. 3A and 3B, the sensor module 320 includes sensor 373. Examples of parameters that a sensor 373 can measure include, but are not limited to, impedance in a portion of the electrical conductor-carrying network, vibration, moisture, and temperature. In this case, the sensor 373 of the sensor module 320 measures impedance in the conduit pipe 312 adjacent to the electrical enclosure 314 (and, thus, the sensor module 320).

The sensor 373 can be disposed in any location on or adjacent to the body 321 of the sensor module 320. In this case, the sensor 373 is disposed on a circuit board 325 (also called, among other names, a wiring board, a printed circuit board, a PCB, a printed wiring board, and a PWB). The location of the sensor 373 relative to the body 321 of the sensor module 320 can vary based on one or more of a number of factors, including but not limited to the parameter measured by the sensor 373, the configuration of the power conversion assembly 353, the size and/or shape of the sensor 373, and the location of the body 321 relative to the electrical conductor-carrying network 310.

In this case, the sensor 373, while disposed on the circuit board 325, is electrically coupled to the body 321 of the sensor module 320, where the body 321 is made of electrically conductive material. Further, the electrical enclosure 314 and the adjacent conduit pipe 312 is also made of electrically conductive material. Since the sensor 373 in this case is configured to measure impedance in the electrical conductor-carrying network 310, the sensor 373 includes a signal generator (which can be directional) and a signal receiver (which can be directional) so that the impedance of the electrical enclosure 314, one or more conduit pipes 312, and/or some other components of the electrical conductor-carrying network 310 can be measured.

The circuit board 325 can include one or more components that allow the sensor module 320 to operate. Examples of such other components can include, but are not limited to, one or more components of the power conversion assembly 353, a hardware processor, field programmable gate arrays (FPGAs), one or more portions of the sensor 373, electrical conductors, terminal blocks, jumpers, and one or more coupling features (e.g., apertures) that allow the circuit board 325 to couple to the body 321 and/or a portion of the electrical conductor-carrying network 310 (e.g., the electrical enclosure 314).

The electrical enclosure 314 can include one or more coupling features 318 that allow the electrical enclosure 314 to couple to another component of the electrical conductor-carrying network 310 (in this case, a conduit pipe 312). For example, in this case, each end of the electrical enclosure 314 includes coupling features 318 that are mating threads disposed on an inner surface of the electrical enclosure 314. These mating threads can be configured to complement the coupling features 317 (in this case, also mating threads) disposed on an outer surface of a conduit pipe 312.

Figure 4:
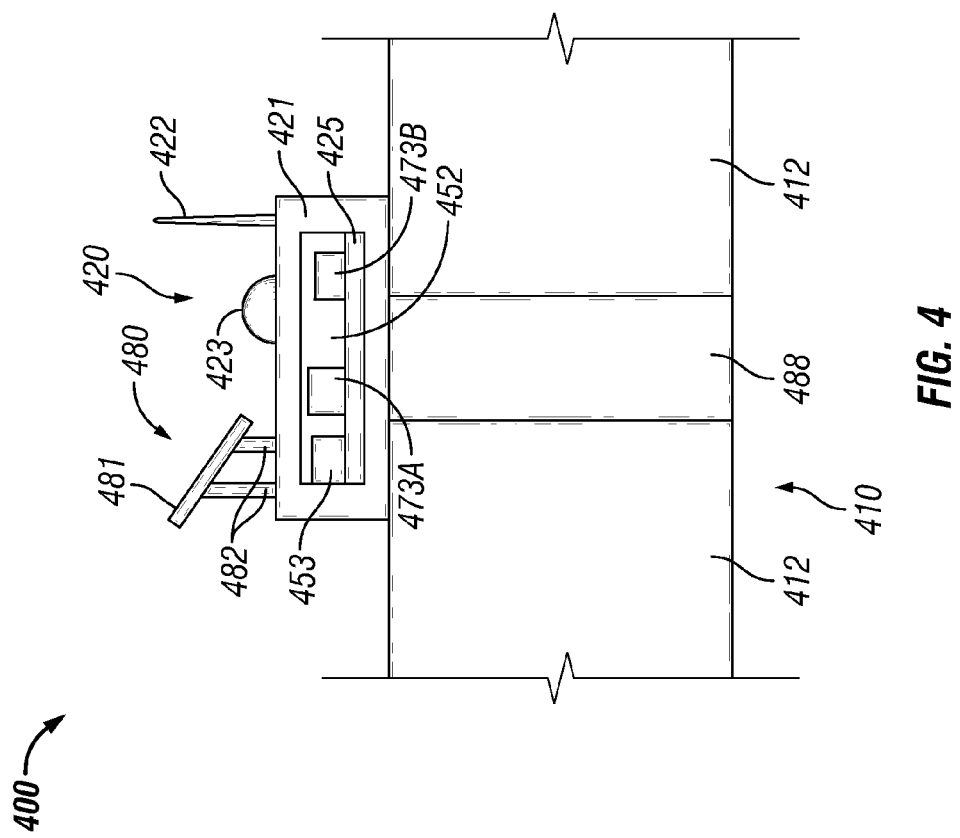
FIG. 4 shows another sensor module in accordance with certain example embodiments.

FIG. 4 shows a portion of an electrical conductor-carrying system 400 (also called an electrical conductor-carrying network herein) that includes another sensor module 420 in accordance with certain example embodiments. The sensor module 420 of FIG. 4 is substantially the same as the sensor module 320 of FIGS. 3A and 3B, except as described below. For example, the sensor module 420 of FIG. 4 includes an antenna 422 and an indicator device 423 that is substantially similar to the antenna 322 and the indicator device 323 of FIGS. 3A and 3B. Referring to FIGS. 1-4, the sensor module 420 is not part of an electrical enclosure, and so the body 421 forms a cavity 452 that is completely enclosed. Inside the cavity 452 formed by the body 421 of FIG. 4 are a circuit board 425, two sensors (sensor 473A and sensor 473B) mounted on the circuit board 425, and a power conversion assembly 453 mounted on the circuit board 425.

The sensor module 420 can have its own power source 480. In this case, the power source 480 is a photovoltaic solar panel 481 disposed on the top outer surface of the body 421 and mounted on supports 482 that are also affixed to the body 421. The power conversion assembly 453 disposed inside the cavity 452 is electrically coupled to the power source 480 to provide the type and amount of power needed by one or more of the other components of the sensor module 420. The sensor module 420 can be secured to the electrical conductor-carrying network 410 by a coupling feature 488. In this case, the coupling feature 488 is a clamp that is disposed around a conduit pipe 412 and tightened against the conduit pipe 412. The coupling feature 488 can be a part of, or a separate device from, the sensor module 420.

Figure 5:
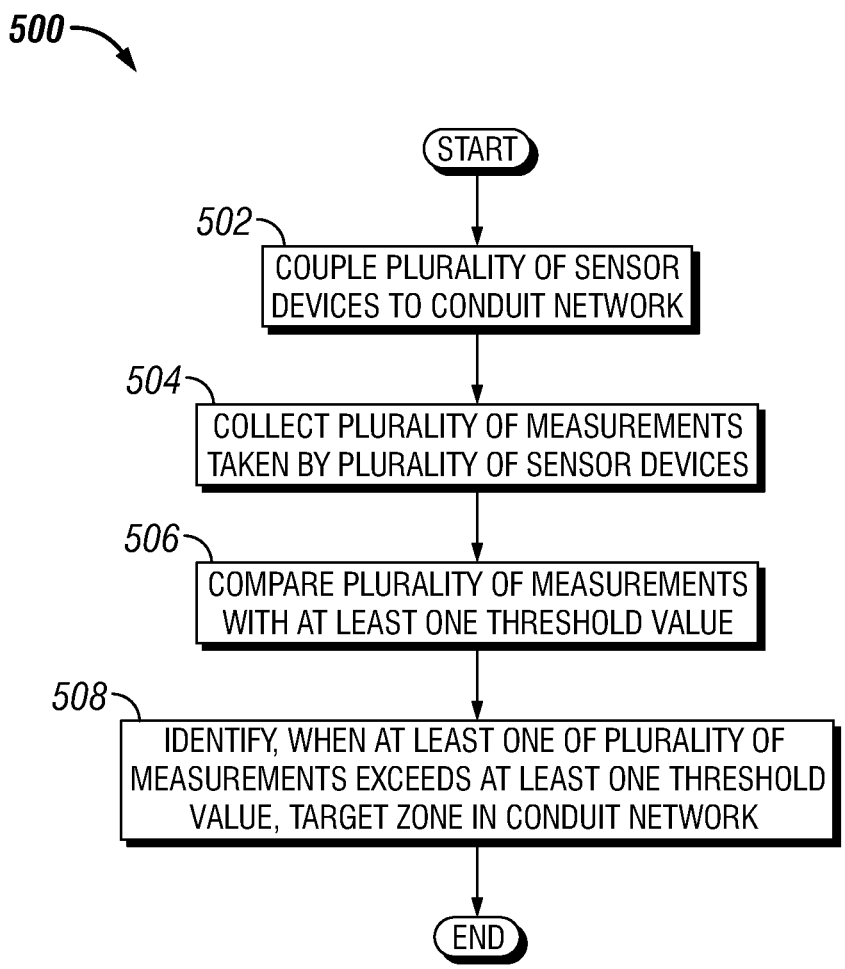
FIG. 5 shows a flowchart of a method for evaluating a grounding state of an electrical conductor-carrying system in accordance with certain example embodiments.

FIG. 5 shows a flowchart of a method 500 for evaluating a grounding state of an electrical conductor-carrying network. While the various steps in this flowchart are presented and described sequentially, one of ordinary skill will appreciate that some or all of the steps may be executed in different orders, may be combined or omitted, and some or all of the steps may be executed in parallel. Further, in one or more of the example embodiments, one or more of the steps described below may be omitted, repeated, and/or performed in a different order.

In addition, a person of ordinary skill in the art will appreciate that additional steps not shown in FIG. 5, may be included in performing this method. Accordingly, the specific arrangement of steps should not be construed as limiting the scope. Further, a particular computing device, as described, for example, in FIG. 6 below, can be used to perform one or more of the steps for the method 500 described below in certain example embodiments.

Referring now to FIGS. 1-5, the example method 500 begins at the START step and proceeds to step 502, where a number of sensor devices (e.g., sensor device 120, sensor device 320) are coupled to the electrical conductor-carrying network 110. Each sensor device 320 can measure one or more parameters related to the electrical conductor-carrying network 110. For example, a sensor device 320 (or more specifically, a sensor 373 of a sensor device 320) can measure at least one impedance in a portion of the electrical conductor-carrying network 110. As another example, a sensor device 320 can measure at least one vibration in a portion of the electrical conductor-carrying network 110. A sensor device 320 can operate using power received, directly or indirectly, from a power source.

In step 504, a number of measurements taken by the sensor devices 120 are collected. In certain example embodiments, the measurements are collected by the control unit 190. The measurements can be collected by the control unit 190 from the sensor devices 120 using wired and/or wireless technology. The measurements can be collected by the control unit 190 continually, periodically, based on the occurrence of an event (e.g., when a measurement is taken), and/or based on some other factor.

In step 506, the measurements are compared with at least one threshold value. In certain example embodiments, the measurements are compared with at least one threshold value by the control unit 190. The threshold values can be stored in a storage repository or some other form of memory. The threshold values can be for instantaneous measurements as well as for measurements that are taken over a period of time and indicate a trend. The threshold values represent a maximum or minimum value of a measurement that is considered safe and acceptable with respect to the grounding state for some or all of the electrical conductor-carrying network 110. A threshold value can be in the same units of measure (e.g., impedance) or different units of measure relative to the measurements taken by the sensor devices 120.

In step 508, a target zone 111 is identified in the electrical conductor-carrying network 110. The target zone 111 can be a part of the electrical conductor-carrying network 110 that includes an adverse electrical condition. The target zone 111 can be identified when at least one of the measurements exceeds a threshold value. The target zone 111 can be identified by the control unit 190 based on the measurements taken by the sensor devices 120. When step 508 is complete, the process can proceed to the END step. Alternatively, when step 508 is complete, the process can revert to step 504 (or some other step in the method 500) and repeat itself in a substantially continuous loop. In other words, the method 500 of FIG. 5 can be performed substantially continuously for some period of time.

Figure 6:
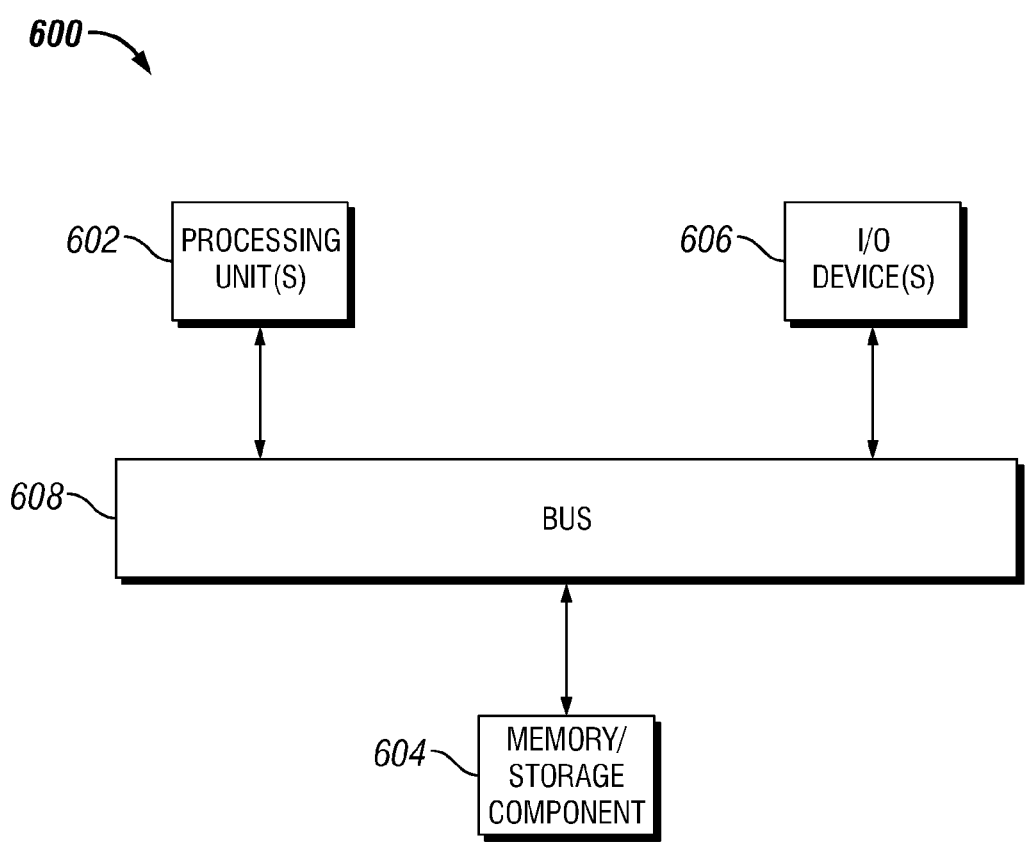
FIG. 6 shows a computing device in accordance with one or more example embodiments.

FIG. 6 illustrates one embodiment of a computing device 600 that implements one or more of the various techniques described herein, and which is representative, in whole or in part, of the elements described herein pursuant to certain example embodiments. Computing device 600 is one example of a computing device and is not intended to suggest any limitation as to scope of use or functionality of the computing device and/or its possible architectures. Neither should computing device 600 be interpreted as having any dependency or requirement relating to any one or combination of components illustrated in the example computing device 600.

Computing device 600 includes one or more processors or processing units 602, one or more memory/storage components 604, one or more input/output (I/O) devices 606, and a bus 608 that allows the various components and devices to communicate with one another. Bus 608 represents one or more of any of several types of bus structures, including a memory bus or memory controller, a peripheral bus, an accelerated graphics port, and a processor or local bus using any of a variety of bus architectures. Bus 608 includes wired and/or wireless buses.

Memory/storage component 604 represents one or more computer storage media. Memory/storage component 604 includes volatile media (such as random access memory (RAM)) and/or nonvolatile media (such as read only memory (ROM), flash memory, optical disks, magnetic disks, and so forth). Memory/storage component 604 includes fixed media (e.g., RAM, ROM, a fixed hard drive, etc.) as well as removable media (e.g., a Flash memory drive, a removable hard drive, an optical disk, and so forth).

One or more I/O devices 606 allow a customer, utility, or other user to enter commands and information to computing device 600, and also allow information to be presented to the customer, utility, or other user and/or other components or devices. Examples of input devices include, but are not limited to, a keyboard, a cursor control device (e.g., a mouse), a microphone, a touchscreen, and a scanner. Examples of output devices include, but are not limited to, a display device (e.g., a monitor or projector), speakers, a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 600 is connected to a network (not shown) (e.g., a local area network (LAN), a wide area network (WAN) such as the Internet, or any other similar type of network) via a network interface connection (not shown) according to some example embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other example embodiments. Generally speaking, the computer system 600 includes at least the minimal processing, input, and/or output means necessary to practice one or more embodiments.

Further, those skilled in the art will appreciate that one or more elements of the aforementioned computer device 600 is located at a remote location and connected to the other elements over a network in certain example embodiments. Further, one or more embodiments is implemented on a distributed system having one or more nodes, where each portion of the implementation (e.g., sensor module 120A, control unit 190) is located on a different node within the distributed system. In one or more embodiments, the node corresponds to a computer system. Alternatively, the node corresponds to a processor with associated physical memory in some example embodiments. The node alternatively corresponds to a processor with shared memory and/or resources in some example embodiments.

Example embodiments provide for diagnosing electrical conductor-carrying system integrity, particularly with respect to a grounding state. Specifically, certain example embodiments allow for a number of sensor modules to be coupled to and distributed throughout an electrical conductor-carrying network of an electrical conductor-carrying system. Example systems, methods, and devices for diagnosing electrical conductor-carrying system integrity can be permanent or temporary installations relative to an electrical conductor-carrying network. Example embodiments can evaluate or diagnose electrical conductor-carrying system integrity by measuring impedance in the conduit network, vibrations experienced by the electrical conductor-carrying network, and/or any other suitable parameters that can affect the grounding state of an electrical conductor-carrying network.

Example embodiments can evaluate an electrical conductor-carrying system based on a single measurement by a sensor device and/or by a series of measurements taken over time. Example embodiments can allow one or more components of an electrical conductor-carrying network (e.g., an electrical enclosure) to comply with applicable standards (e.g., NEMA 7 enclosure) and/or regulations. Example embodiments can easily be installed and maintained by a user. Example sensor modules can be self-calibrating. Example sensor devices can be moved around a facility with one or more electrical conductor-carrying networks or from one facility with an electrical conductor-carrying network to another facility with a conduit network. Example embodiments can identify a target zone within an electrical conductor-carrying network where an adverse electrical condition is occurring or is likely to occur in the near future.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A system for diagnosing ground integrity of a pipe network, the system comprising:
    the pipe network comprising a plurality of pipes mechanically coupled to each other, wherein the plurality of pipes is made of electrically conductive material;
    a plurality of sensor modules coupled to and distributed throughout the pipe network; and
    a control unit communicably coupled to the plurality of sensor modules,
    wherein each of the plurality of sensor modules takes measurements of at least one impedance in the plurality of pipes at a location among a plurality of locations in the pipe network,
    wherein the control unit uses the measurements made by the plurality of sensor modules at the plurality of locations to identify a target zone within the pipe network in which the ground integrity is degraded,
    wherein the measurements of the at least one impedance indicate the ground integrity of a pipe relative to other pipes, and wherein the measurements of the at least one impedance made by the plurality of sensor modules are made independent of how power is provided to the plurality of sensor modules to perform such measurements and independent of content disposed within the pipe network.

2. The system of claim 1, further comprising:
    at least one electrical cable disposed within the plurality of pipes, wherein the plurality of sensor modules operate based on power flowing through the at least one electrical cable.

3. The system of claim 2, wherein a first sensor module of the plurality of sensor modules comprises an inductor disposed around the at least one electrical cable, wherein the inductor provides the power to the first sensor module.

4. The system of claim 3, wherein the pipe network comprises a removable cover, wherein the first sensor module is accessible when the removable cover is removed from the pipe network.

5. The system of claim 4, wherein the first sensor module replaces the removable cover.

6. The system of claim 4, wherein the removable cover is part of an existing enclosure of the pipe network.

7. The system of claim 1, wherein at least one of the plurality of sensor modules are communicably coupled to the control unit using wireless technology.

8. The system of claim 1, wherein the plurality of sensor modules take the measurements of the at least one impedance in the plurality of pipes over a period of time.

9. The system of claim 8, wherein the plurality of measurements indicate corrosion in the target zone of the pipe network, wherein the target zone is specifically identified within the pipe network.

10. The system of claim 8, wherein the plurality of measurements indicate a faulty ground connection in the target zone of the pipe network.

11. The system of claim 1, wherein at least one of the plurality of sensor modules is self-calibrating.

12. The system of claim 1, wherein the plurality of sensor modules are movable by a user between the pipe network and another pipe network.

13. The system of claim 1, wherein the pipe network is located in a hazardous environment.

14. The system of claim 1, wherein the control unit is communicably coupled to an additional control unit used with another plurality of sensor modules in another pipe network.

15. The system of claim 1, wherein at least one of the plurality of sensor modules wraps around a pipe of the pipe network.

16. The system of claim 1, wherein the plurality of pipes is void of non-electrically-conductive material.

* * * * *